`United States Patent` [19]

White et al.

[11] Patent Number: 5,635,495
[45] Date of Patent: Jun. 3, 1997

[54] PYRIMIDINE BISPHOSPHONATE ESTERS AND (ALKOXYMETHYLPHOSPHINYL) ALKYL PHOSPHONIC ACIDS AS ANTI-INFLAMMATORIES

[75] Inventors: David R. White; Edward L. Fritzen, Jr., both of Kalamazoo, Mich.

[73] Assignee: The Upjohn Company, Kalamazoo, Mich.

[21] Appl. No.: 416,797

[22] PCT Filed: Sep. 20, 1993

[86] PCT No.: PCT/US93/08626

§ 371 Date: Apr. 6, 1995

§ 102(e) Date: Apr. 6, 1995

[87] PCT Pub. No.: WO94/09017

PCT Pub. Date: Apr. 28, 1994

Related U.S. Application Data

[63] Continuation-in-part of Ser. No. 959,316, Oct. 9, 1992, abandoned, and Ser. No. 958,986, Oct. 9, 1992, abandoned.

[51] Int. Cl.$^6$ .............. A61K 31/675; C07F 9/6512; C07F 9/6561
[52] U.S. Cl. .............. 514/81; 544/117; 544/122; 544/123; 544/232; 544/243; 544/244; 514/86
[58] Field of Search ................ 544/243, 244, 544/117, 123; 514/81, 86

[56] References Cited

U.S. PATENT DOCUMENTS

| | | | |
|---|---|---|---|
| 3,683,080 | 8/1972 | Francis | 424/204 |
| 4,696,920 | 9/1987 | Bentzen et al. | 514/90 |
| 4,746,654 | 5/1988 | Breliere et al. | 514/108 |
| 5,397,774 | 3/1995 | Nugent et al. | 514/81 |

FOREIGN PATENT DOCUMENTS

| | | |
|---|---|---|
| 51534/85 | of 0000 | Australia . |
| 186405 | 7/1986 | European Pat. Off. . |
| 0298553 | 11/1989 | European Pat. Off. . |
| 354806 | 2/1990 | European Pat. Off. . |
| 3626058 | of 0000 | Germany . |
| 3719513 | 6/1987 | Germany . |
| 9203451 | 3/1992 | WIPO . |
| 92-14474 | 9/1992 | WIPO . |
| 9301198 | 1/1993 | WIPO . |
| 93-11786 | 6/1993 | WIPO . |

OTHER PUBLICATIONS

Alkylation of 5,7-dimethyl pyrazolo[1,5-a]pyrimidines, American Chemical Society Spring meeting (Jun. 8, 1988), PD 7244-88-021.

Ebetino, F.H. et al., "Recent Work on the Synthesis of Phosphonate–Containing, Bone–Active Heterocycles", Heterocycles 30(2):855–62 (1990).

Teulade, M–P and P. Savignac, "Carbanions Phosphonates α–Lithiés: Synthèse, Basicité Comparée, et Stabilitéà L'Autocondensation," J. of Organometalic Chem. 312:283–95 (1986).

Gompper, *Chemical Abstracts* vol. 54, No. 9955b (1960).

Gompper, *Chem. Ber.* vol. 93, pp. 198–209 (1960).

Abstract for DE 3719513 (Dec. 22, 1988).

Abstract for DE 3,626,058 (Feb. 11, 1988).

*Primary Examiner*—Emily Bernhardt
*Attorney, Agent, or Firm*—Donald L. Corneglio

[57] ABSTRACT

Compounds useful in the treatment of inflammation structurally represented as wherein $X, X^1$ and R groups are as herein defined.

14 Claims, No Drawings

PYRIMIDINE BISPHOSPHONATE ESTERS AND (ALKOXYMETHYLPHOSPHINYL) ALKYL PHOSPHONIC ACIDS AS ANTI-INFLAMMATORIES

CROSS-REFERENCE TO RELATED APPLICATIONS

This application is the phase of international application PCT/US93/08626, filed Sep. 20, 1993, which was a continuation-in-part of U.S. Ser. No. 07/959,316, filed Oct. 9, 1992, and U.S. Ser. No. 07/958,986, filed Oct. 9, 1992, both abandoned.

BACKGROUND OF THE INVENTION

The present invention is directed toward pyrazolopyrimidine (Formula 1) and pyrimidinyl (Formula 2) (alkoxymethylphosphinyl)alkyl phosphonic acids, pyrimidine bisphosphonates (Formula 3) and their pharmaceutically acceptable salts which are useful as anti-inflammatories, anti-arthritic agents and in the case of Formula 3, Ca-channel blockers useful in cardiovascular diseases.

The subject compounds are also useful for treating arthritis and its related symptoms such as inflammation and prevention of excessive bone regrowth and remodeling while showing a decreased bone affinity. One class of such compounds which still maintain anti-resorptive activity are the phosphinyl-phosphonic acids prepared by Ebitino et al., cited below.

DESCRIPTION OF THE RELATED ART

The following related art are bisphosphonic tetraester or acids directed toward Formulas 1 and 2:

U.S. Pat. No. 4,746,654 discloses bisphosphonates useful as anti-inflammatory agents, Australian Patent A-51534/85 discloses bisphosphonates useful in treating abnormal calcium and phosphorous metabolism and useful in treating arthritis.

U.S. Pat. No. 3,683,080 discloses polyphosphonates, in particular diphosphonates useful in inhibiting anomalous deposition and mobilization of calcium phosphate in animal tissue.

DE 3,719,513-A (Derwent 89-000580/01) discloses diphosphonic acid derivatives useful in treatment of disorders of calcium metabolism.

With respect to Formula 1 compounds, the alkylation of 5,7-dimethyl pyrazolo[1,5-a]pyrimidines was disclosed at the American Chemical Society spring meeting on Jun. 9, 1988, PD 7244-88-021.

Yamanouchi has published imidazo[1,2-a]pyridines and imidazo[1,2-a]imidazoles (EP 354-806 A2, Feb. 14, 1990). Boehringer Mannheim DE 3626-058 A1 discloses heteroaromatic diphosphonates bound to a diphosphonate.

The following related an disclose bisphosphonic tri-esters or acid with an alkyl substituent:

Savignac, et al., *Carbanions Phosphonates*, J. of Organometallic Chem., 312:283–95 (1986); and Ebetino, F. H., "Phosphate Containing Bone Active Heterocycles," Heterocycles 30(2):855–62 (1990).

The following related art are directed toward compounds of Formula 3:

AU-A-5153485 (publication date Jun. 26, 1986) (EP 186 405) discloses pyrimidine bisphosphonates related to the compounds of the present invention. The substituents on the pyrimidine ring, however, are hydrogen, methyl, amino, methoxy, nitro, hydroxy, and combinations thereof; whereas, the subject invention precludes these substituents in favor of the $X^1$ group as defined below.

U.S. Pat. No. 4,696,920 discloses 1,3 diphosphonates useful for the treatment of cardiovascular diseases.

SUMMARY OF THE INVENTION

In one aspect, the subject invention consists of pyrazolopyrimidine (Formula 1) and pyrimidinyl (Formula 2) (alkoxymethylphosphinyl)alkyl phosphonic esters, acids and their pharmaceutically acceptable salts, which are structurally represented as:

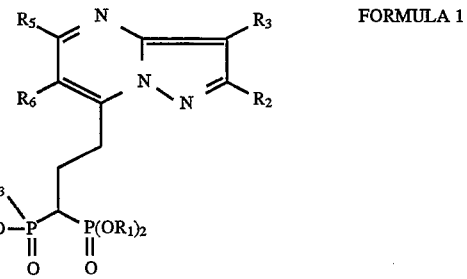

FORMULA 1

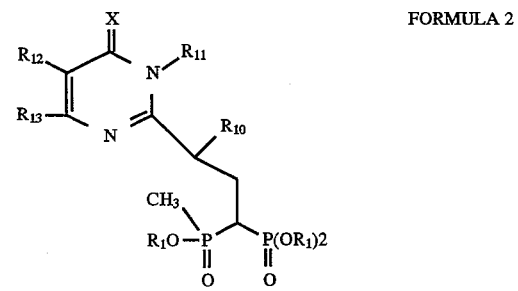

FORMULA 2 wherein X is O or S;

each $R_1$ is the same or different and is selected from the group consisting of H, Na, K, tromethamine, $C_1$–$C_6$ alkyl, $CH_2$-phenyl, phenyl (optionally substituted with 1 to 5 $NO_2$, halo, or $C_1$–$C_4$ alkyl), or both $R_1$'s on the same phosphorus atom are taken together to be —$CH_2$—$CH_2$—, —$CH_2$—$CH_2$—$CH_2$—, or —$CH_2$—$C(CH_3)_2$—$CH_2$— whereby a heterocyclic ring is formed;

$R_2$ is hydrogen, $C_1$–$C_6$ alkyl, benzoyloxy, benzyloxy, $C_1$–$C_6$ alkoxy, phenoxy, $C_3$–$C_7$ cycloalkyl, phenyl (optionally substituted with 1 or 2 phenyls, or 1 to 5 halo, $NO_2$, CN, $CF_3$, $C_1$–$C_{10}$ alkyl, $C_3$–$C_7$ cycloalkyl, $C_1$–$C_6$ alkoxy or $C_1$–$C_6$ alkylthio), 2-, 4- or 5-pyrimidyl (optionally substituted with 1 or 2 phenyls, or 1 to 3 halo, $NO_2$, CN, $CF_3$, $C_1$–$C_{10}$ alkyl, $C_3$–$C_7$ cycloalkyl, $C_1$–$C_6$ alkoxy, or $C_1$–$C_6$ alkylthio), 2-, 3- or 4-pyridyl (optionally substituted with 1 or 2 phenyls, or 1 to 4 halo, $NO_2$, CN, $CF_3$, $C_1$–$C_{10}$ alkyl, $C_3$–$C_7$ cycloalkyl, $C_1$–$C_6$ alkoxy or $C_1$–$C_6$ alkylthio), 1- or 2-naphthalenyl (optionally substituted with 1 or 2 phenyls, or 1 to 7 halo, $NO_2$, CN, $CF_3$, $C_1$–$C_{10}$ alkyl, $C_3$–$C_7$ cycloalkyl, $C_1$–$C_6$ alkoxy or $C_1$–$C_6$ alkylthio);

$R_3$ is H, CN, $CO_2R_1$, $COR_2$, $CON(R_5)_2$, halo, $NO_2$, CN, $CF_3$, $C_1$–$C_{10}$ alkyl, $C_3$–$C_7$ cycloalkyl, or phenyl;

$R_5$ is H, $C_1$–$C_6$ alkyl or $C_3$–$C_7$ cycloalkyl;

$R_6$ is H, halo, or $C_1$–$C_6$ alkyl;

$R_{10}$ is H, $C_1$–$C_6$ alkyl, $C_3$–$C_7$ cycloalkyl, or phenyl (optionally substituted with 1 or 2 phenyls, or 1 to 5 halos, $NO_2$, CN, $CF_3$, $C_1$–$C_{10}$ alkyl, $C_3$–$C_7$ cycloalkyl, $C_1$–$C_6$ alkoxy or $C_1$–$C_6$ alkylthio;

$R_{11}$ is H, $C_1$-$C_6$ alkyl, $C_3$-$C_7$ cycloalkyl, allyl, $CH_2OR_4$, $CH_2$-phenyl, or phenyl (optionally substituted with 1 to 5 $NO_2$, halos, or $C_1$-$C_4$ alkyl);

$R_{12}$ is H, $C_1$-$C_6$ alkyl, halo, $NO_2$;

$R_{13}$ is hydrogen, $C_1$-$C_6$ alkyl, $C_3$-$C_7$ cycloalkyl, or phenyl (optionally substituted with 1 to 2 phenyls, or 1 to 5 halos, $NO_2$, CN, $CF_3$, $C_1$-$C_{10}$ alkyl, $C_3$-$C_7$ cycloalkyl, $C_1$-$C_6$ alkoxy or $C_1$-$C_6$ alkylthio), 2-, 3- or 4-pyridyl (optionally substituted with 1 to 2 phenyls, or 1 to 4 halos, $NO_2$, CN, $CF_3$, $C_1$-$C_{10}$ alkyl, $C_3$-$C_7$ cycloalkyl, $C_1$-$C_6$ alkoxy or $C_1$-$C_6$ alkylthio), 1- or 2-naphthalenyl (optionally substituted with 1 to 2 phenyls, or 1 to 7 halos, $NO_2$, CN, $CF_3$, $C_1$-$C_{10}$ alkyl, $C_3$-$C_7$ cycloalkyl. $C_1$-$C_6$ alkoxy or $C_1$-$C_6$ alkylthio), piperidyl, morpholyl, pyrrolidyl. $N(R_5)_2$. $NHC(O)R_{14}$ or $NHC(O)OR_{14}$; and $R_{14}$ is $C_1$-$C_6$ alkyl, $C_3$-$C_7$ cycloalkyl, allyl, $CH_2$-phenyl, or phenyl (optionally substituted with 1 to 5 $NO_2$, halos, or $C_1$-$C_4$ alkyl).

In another aspect, the subject invention is phosphonetic esters, acids and their pharmaceutically acceptable salts which are structurally represented by Formula 3:

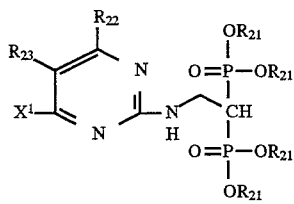

wherein $R_{21}$ are the same or different and are selected from the group consisting of H, $C_1$-$C_6$ alkyl, $C_3$-$C_8$ cycloalkyl, $CH_2Ph$, or where both $R_{21}$'s on the same phosphorus atom taken together are —$CH_2$—$CH_2$—, —$CH_2$—$CH_2$—$CH_2$—, or —$CH_2$—$C(CH_3)_2$—$CH_2$— whereby a heterocyclic ring is formed;

$R_{22}$ is H, $C_1$-$C_6$ alkyl, $C_3$-$C_8$ cycloalkyl or phenyl (optionally substituted with 1 or 2 phenyls, or 1 through 5 F, Cl, Br, I, $NO_2$, CN, $CF_3$, $C_1$-$C_{10}$ alkyl, $C_3$-$C_7$ cycloalkyl, OH, SH, $NH_2$, $C_1$-$C_6$ alkoxy or $C_1$-$C_6$ alkylthio);

$R_{23}$ is H, phenyl, F, Cl, Br, I, $C_1$-$C_{10}$ alkyl, $C_3$-$C_7$ cycloalkyl, $C_1$-$C_6$ alkoxy, $C_1$-$C_6$ alkylthio, or $NH_2$;

$X^1$ is $OR_{24}$, $SR_{24}$, morpholinyl, piperazinyl, piperidinyl, imidazolidinyl, pyrazolidinyl, isoxazolyl, pyrrolyl, imidazolyl, pyrazolyl, pyridyl, pyrazinyl, pyrimidinyl or pyridazinyl; and $R_{24}$ is phenyl (optionally substituted with 1 or 2 phenyls, or 1 through 5 F, Cl, Br, L $NO_2$, CN, $CF_3$, $C_1$-$C_{10}$ alkyl, $C_3$-$C_7$ cycloalkyl, OH, SH, $NH_2$, $C_1$-$C_6$ alkoxy or $C_1$-$C_6$ alkylthio).

In the case where "$X^1$ is one of the listed heterocyclic rings, the attachment point is at an available ring nitrogen.

More preferably, compounds of Formula 3 are where $R_{21}$ are the same or different and are selected from the group consisting of $C_1$-$C_6$ alkyl, $C_3$-$C_8$ cycloalkyl, $CH_2Ph$, or where both $R_{21}$'s on the same phosphorus atom taken together are —$CH_2$—$CH_2$—, —$CH_2$—$CH_2$—$CH_2$— or —$CH_2$—$C(CH_3)_2$—$CH_2$— whereby a heterocyclic ring is formed. When $R_{21}$ is not hydrogen, the compounds are calcium channel blockers useful for the treatment of unstable angina, hypertension, control of heart rate, atrial fibrillation, atrial flutter, and paroxysmal supraventricular tachycardia.

In another aspect, the present invention comprises the use of these compounds in humans and lower animals, patients, as a safe and effective treatment of diseases characterized by abnormal phosphate and calcium metabolism, and as a treatment of inflammation. These diseases include osteoporosis, Paget's disease, periodontal disease, rheumatoid arthritis, osteoarthritis, neuritis, bursitis, soft tissue mineralization disorders, ankylosing spondylitis, atherosclerosis, multiple myeloma of bone, metastic bone disease, and mitral valve calcification.

A method for treating inflammation comprises administering to an animal or human patient in need of such treatment an anti-inflammatory effective amount of a compound of Formula 1.2 or 3. Routes of administration include oral, intramuscular, intravenous, transdermal, intra-articular. subcutaneous, or intraperitoneal. An effective amount is an amount whereby the symptoms of inflammation or arthritis such as pain and discomfort are relieved or reduced or mobility of the affected area is increased. A typical dosage is about 0.001 mg to 1.0 gram with dose determined by the particular mode of administration, use and frequency of administration.

DETAILED DESCRIPTION OF THE INVENTION

The present invention comprises pyrazolopyrimidine (Formula 1 ) and pyrimidinyl (Formula 2) (alkoxymethylphosphinyl)alkyl phosphonic and bisphosphonic (Formula 3) esters, acids and their pharmaceutically acceptable salts, which are structurally represented by Formula 1, 2 and 3, respectively. The compounds are particularly useful in the treatment of arthritis and its associated symptoms such as inflammation and excessive bone growth or remodeling. These diseases include osteoporosis, Paget's disease, periodontal disease, rheumatoid arthritis, osteoarthritis, neuritis, bursitis, soft tissue mineralization disorders, ankylosing spondylitis, atherosclerosis, multiple myeloma of bone, metastic bone disease, and mitral valve calcification. In particular, the compounds of Formula 3 do not inhibit cyclooxygenase or lipoxygenase metabolism of arachidonic acid and so constitute a novel method of treating inflammation.

In Formulas 1, 2 and 3, the variable designations are further defined as follows.

The carbon content of various hydrocarbon containing moieties is indicated by a prefix designating the minimum and maximum number of carbon atoms in the moiety, i.e., the prefix $C_i$-$C_j$ defines the number of carbon atoms present from the integer "i" to the integer "j" inclusive. Thus, $C_1$-$C_3$ alkyl refers to alkyl of 1–3 carbon atoms, inclusive, or methyl, ethyl, propyl, and isopropyl.

With respect to the above, $C_1$-$C_6$ alkyl is methyl, ethyl, propyl, butyl, pentyl, hexyl, and isomeric forms thereof. $C_3$-$C_7$ cycloalkyl is cyclopropane, cyclobutane, cyclopentane, cyclohexane, cycloheptane and isomeric forms thereof.

The term "halo" includes fluoro, chloro, bromo and iodo and "Ph" is phenyl.

$C_1$-$C_8$ alkylthio are methylthio, ethylthio, propylthio, butylthio, pentylthio, hexylthio, heptylthio, octothio, and isomeric forms thereof.

$C_1$-$C_8$ alkoxy are methoxy, ethoxy, propoxy, butoxy, pentoxy, hexoxy, heptoxy, octooxy, and isomeric forms thereof.

Pharmaceutically acceptable salts means salts useful for administering the compounds of this invention and include potassium, sodium hydrochloride, hydrobromide, hydroiodide, sulfate, phosphate, acetate, propionate, lactate, mesylate, maleate, malonate, succinate, tartrate, citric acid and the like. These salts may be in hydrated form.

The pyrazolopyrimidine (alkoxymethylphosphinyl)alkyl phosphonic esters, acids and derivatives (Formula 1) useful as anti-inflammatories and antiarthritics are prepared as follows in Examples 1–12. The general pyrazolopyrimidine heterocyclic ring structure can be prepared by procedures well known in the art. For example, the synthesis of pyrazolo [1,5-a]pyrimidines is described by M. H. Elnagdi, G. E. H. Elgemeie, and M. R. H. Elmoghayar in Advances in Heterocyclic Chemistry, Vol. 41, pg 319; M. R. H. Elmoghayar et al., Pyrimidine Derivatives and Related Compounds, Arch. Pharm. (Weinheim), 316, pp 697–702 (1983); and T. Novinson et al., 3-Substituted 5,7-Dimethylpyrazolo(1,5-a) pyrimidines, J. Meal. Chem., 17, pp 645–48 (1974).

The pyrimidinyl (alkoxymethylphosphinyl)alkyl phosphonic esters, acids and derivatives (Formula 2) useful as an anti-inflammatory and antiarthritic are prepared as follows and as described in Examples 13–16. The synthesis of 4-pyrimidinones is well known to those skilled in the art. Briefly, a β-keto ester is treated with acetamidine hydrochloride in the presence of base to form the parent heterocycle. The base can be sodium hydroxide, potassium carbonate, sodium methoxide, or sodium ethoxide. The reaction can be run neat or the solvent can be ethanol or methanol. N-alkylated derivatives are synthesized by treatment of the parent compound with an electrophile in the presence of base, such as potassium carbonate, sodium hydride, or potassium fluoride.

In Formula 3, when $R_{21}$ is not hydrogen, then the compounds are calcium channel blockers useful for the treatment of unstable angina, hypertension, control of heart rate, atrial fibrillation, atrial flutter, and paroxysmal supraventricular tachycardia.

Both pyrazolopyrimidines and 4-pyrimidones (Formulas 1 and 2) can be deprotonated using any number of strong bases to form stabilized carbanions. Such carbanions after a standard workup can then be added to 1-(Ethoxymethylphosphinyl)-1-ethanyl phosphonic acid, diethyl ester to give structures of the type illustrated by Formula 1 and Formula 2.

1-(Ethoxymethylphosphinyl)-1-ethenyl phosphonic acid diethyl ester is prepared from (ethoxymethylphosphinyl) methyl phosphonic acid, diethyl ester using known chemistry. One method of preparing (ethoxymethylphosphinyl) methyl phosphonic acid is the Arbuzov reaction of diethyl iodomethylphosphonate with diethylmethylphosphite. A more preferred route is the dimerization of the lithium anion of dialkyl methylphosphonates as reported by Savignac et at.

The above (alkoxyphosphinyl)alkyl phosphonate then undergoes a nucleophilic addition with stabilized anions to afford Formula 1 or 2 compounds. Typically, (ethoxymethylphosphinyl)-1-ethenylphosphonic acid, diethylester is reacted in the presence of a carbanion of the heterocyclic ring structures of Formula 1 or 2. The carbanion is formed at −70° C. to 80° C. and the (alkoxyphosphinyl) alkyl phosphonate is added to the reaction mixture and maintained for about 30 minutes, then allowed to warm to ambient. The reaction mixture is quenched with saturated aqueous ammonium chloride and extracted with chloroform. Standard work-up affords the product which can be purified by chromatography. The examples further demonstrate this procedure.

Preferred compounds of Formula 3 are identified by letter and include:

a) (2-((4-(2-fluoro-6-nitrophenoxy)-6-methyl-2-pyrimidinyl)amino)ethylidene)bis(2,2'-(5,5-dimethyl-2,2'-dioxide-1,3,2-dioxaphosphorphinane));

b) (2-((4-(2,4-difluorophenoxy)-6-methyl-2-pyrimidinyl)amino)ethylidene)bis(2,2'-(5,5-dimethyl-2,2'-dioxide-1,3,2-dioxaphosphorphinane));

c) (2-((4-(4-morpholinyl)-6-methyl-2-pyrimidinyl)amino)ethylidene)bis(2,2'-(5,5-dimethyl-2,2'dioxide-1,3,2-dioxaphosphorphinane));

d) (2-((4-(2-,4-dibromophenoxy)-6-methyl-2-pyrimidinyl)amino)ethylidene)bis(2,2'(5,5-dimethyl-2,2'-dioxide-1,3,2-dioxaphosphorphinane));

e) (2-((4-(4-cyanophenoxy)-6-methyl-2-pyrimidinyl)amino)ethylidene)bis(2,2'(5,5-dimethyl-2,2'dioxide-1,3,2-dioxaphosphorphinane));

f) (2-((4-2,4-dichlorophenoxy-6-methyl-2-pyrimidinyl)amino)ethylidene)bisphosphonic acid tetraethyl ester, g) (2-((4-(4-piperidinyl)-6-methyl-2-pyrmidinyl)amino)ethylidene)bis(2,2'-(5,5-dimethyl-2,2'dioxide-1,3,2-dioxaphosphorphinane));

h) (2-((4-(3,4-dichlorophenoxy)-6-methyl-2-pyrimidinyl)amino)ethylidene)bis(2,2'-(5,5-dimethyl-2,2'-dioxide-1,3,2-dioxaphosphorphinane));

i) (2-((4-(phenylthio)-6-methyl-2-pyrimidinyl)amino)ethylidene)bis(2,2'-(5,5-dimethyl-2,2'dioxide-1,3,2-dioxaphosphorphinane));

j) (2-((4-(3-chlorophenoxy)-6-methyl-2-pyrimidinyl)amino)ethylidene)bis(2,2'-(5,5-dimethyl-2,2' dioxide-1,3,2-dioxaphosphorphinane));

k) (2-((4-(2,4-dichlorophenoxy)-6-methyl-2-pyrimidinyl)amino)ethylidene)bisphosphonic acid. tetraethyl ester, and l) (2((4-(methyl)-6-methoxy-2-pyrimidinyl)amino)ethylidene)bis(2,2'-(5,5-dimethyl-2,2'-dioxide-1,3,2-dioxaphosphorphine)).

Typically, the Formula 3 compounds are prepared by selecting the appropriately substituted 2-amino pyrimidines synthesized by means familiar to those skilled in the art, and involve the reaction of 6-halo-2-amino pyrimidines with the desired alkoxide, phenoxide, thiophenoxide, or amine in an inert solvent such as toluene, THF, DMSO, or DMF or the solvent can be the corresponding alcohol, phenol, or thiophenol. Temperatures can range between 0° C. and reflux. The preferred temperature is room temperature. If the alcohol is low molecular weight, the preferred solvent is the corresponding alcohol or else is DMF. The products are isolated by dilution with water, and collection of the solid. This material can be recrystallized if needed.

The bisphosphonates are synthesized through the reaction of the above 2-amino pyrimidines with vinylidene bisphosphonate esters, which have previously been described in published PCT Application WO 9012 017 and by Degenhardt, C. R.; Burdsall, D. C. J. Org.Chem., 51, 3488–3490 (1986). The reaction occurs in an inert solvent, such as THF, benzene, toluene, or xylene at elevated temperatures. It is preferred that the reaction be run in toluene at reflux. Experimental details are contained in the Examples.

The synthesis of the corresponding acid is accomplished by a procedure which is well known to those skilled in the art. Typically, the tetraester is treated with trimethylsilyl bromide in an inert solvent such as chloroform or methylene chloride, followed by aqueous workup to isolate the acid.

Compounds of Formula 3 and a compound of Formula 2 have been tested in a Delayed Type Hypersensitivity Granuloma Assay (DTH GRA) model for inflammation. This assay is described by Dunn, C. J. et al., "Development of a delayed-type hypersensitivity granuloma model in the mouse for the study of chronic immune-mediated inflammatory disease," Agents and Actions, 27, ¾ (1989) and "Murine Delayed-Type Hypersensitivity Granuloma," Int. J. Immunopharmc., 12, 8, 899–904 (1990).

Briefly, mBSA-sensitized mice have a DTH granuloma (DTH GRA) lesion induced by subcutaneously implanting a mBSA-soaked filter which is excised after nine days. Compounds are administered to the mice to determine their effect on the lesions. The results are recorded as percent inhibition. The larger the inhibition, the more effective the compound. Inhibition of 10 to 20% is considered to indicate anti-granuloma activity. Greater than 30% inhibition is good activity.

The compounds are scored as having anti-inflammatory activity at 10–20% inhibition and good activity at greater than 30% inhibition. The compound of Formula 2 tested was 1-((ethoxy-methylphosphinyl))-4-(3-methyl-6-phenyl-4 (3H)-pyrimidinone-2-yl)-butane phosphonic acid diethyl ester, Example 16 and the DTH GRA data obtained for this compound was 44.4%.

The biological results for compounds of Formula 3 are shown in Table 1.

TABLE 1

| Compound | Dose (mg/kg) PO | % Inhibition Wet Weight | Dry Weight |
| --- | --- | --- | --- |
| Ex. 25 (k) | 100* | 40.5 | 39.6 |
| Ex. 17 (a) | 10 | 47.9 | 39.0 |
| Ex. 26 (l) | 10 | 41.9 | 44.8 |
| Ex. 18 (b) | 10 | 70.6 | 58.3 |
| Ex. 21 (c) | 10 | 68.6 | 62.5 |
| Ex. 19 (d) | 10 | 12.1 | 25.0 |
| Ex. 20 (e) | 10 | 27.4 | 41.8 |
| (f) | 10 | 45.9 | 39.7 |

*Compound was administered sc

These compounds were also tested in an in vitro model which identifies calcium channel blocking activity. In this test, adherent human dermal fibroblasts (CRL 1445, ATCC, Bethesda, Md.) were allowed to attach to glass cover slips placed in 6 well culture plates. Cultures were maintained in DMEM supplemented with antibiotics and 10% fetal bovine serum (FBS) until confluent.

The fibroblasts were washed once with Dulbecco's phosphate buffered saline to remove the culture medium and FBS. The calcium probe, INDO-1 AM (2 mM) in RPMI 1640 without phenol red and supplemented with 10 mM hepes and 2 mM glutamine was added to the cells for 1 hour at 37° C. The cells were washed twice with RPMI1640 and remained in this medium until calcium measurements were obtained with the Meridian ACAS digital image microscope.

The cover slip with the attached fibroblasts was placed in a chamber with 1 ml of RPMI on the microscope stage, and maintained at 37° C. The cells were exposed to a laser beam set at 310 nm and fluorescent emission was measured at 485 nm and 405 nm. Baseline resting calcium levels of the fibroblasts were measured for 30 seconds after which 40 mM KCl was added to the medium in the holder. Data was collected at 40 second intervals for a total of 300 to 400 seconds. Maximal calcium influx is usually reached within 40 seconds after the addition of KCl, and begins to slowly decrease to ~50% of the maximal level. The intracellular calcium concentrations remain elevated for at least 400 seconds.

In order to measure the inhibitory effect of the test compounds on changes in intracellular calcium, the compound was added to the cells maintained in RPMI medium for a minimum of 20 minutes before the fibroblast membranes were depolarized with KCl as outlined above. The mean increase in intracellular calcium was then compared to control fibroblasts which had been pretreated for similar lengths of time with DMSO and exposed to KCl. A calcium standard curve was obtained on the day of the experiments in order to generate absolute intracellular calcium concentrations if needed.

Two known calcium channel blockers, D600 and nifedipine were also tested to compare the relative efficacies of the "standard" compounds with the novel diphosphonates. For instance, D600 (available from the Sigma Co., St. Louis, Mo.) inhibited calcium influx into a cell by 83 to 100% at $10^{-5}$ molar concentration. The biological results for calcium channel activity are shown in Table 2. The Control is a sub-structure of Example 9 (k) not having the bisphosphonate teralkyl ester portion. Therefore, the results show that the bisphosphonate teraalkyl ester is required for biological activity.

TABLE 2

| Compound | % Inhibition Mean SD Concentration of Compound | | |
| --- | --- | --- | --- |
| | $10^{-5}$M | $10^{-6}$M | $10^{-7}$M |
| Control Ex. 25 (k) | 12 (n = 2) 92 ± 5 (n = 21) | 75 ± 9 (n = 6) | 35 ± 19 (n = 6) |

The subject invention provides a method for treating intimation by administering to an animal or human patient in need of either treatment a therapeutically effective amount of a compound of Formula 1, 2 or 3. Routes of administration include oral, intramuscular, intravenous, transdermal, intra-articular, subcutaneous, or intraperitoneal. An effective amount is an amount whereby the symptoms such as pain and discomfort are relieved or reduced, and for inflammation or arthritis, where mobility of the affected area is increased. A typical dosage is about 0.001 mg to 1.0 gram with dose determined by the particular mode of administration, use and frequency of administration.

The compounds can be administered intravenously, intramuscularly, topically, transdermally such as by skin patches, bucally or orally to humans or other animals. The compositions of the present invention can be presented for administration in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions, the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The dry lyophilized powder can then be sealed in the vial and reconstituted prior to use.

The following Examples 1–16 are pyrazolopyrimidine (Formula 1) and pyrimidinyl (Formula 2) (alkoxymethylphosphinyl)alkyl phosphonic esters and acids.

Example 1

1-(Ethoxymethylphosphinyl)-3-Cyano-2,5-dimethyl-pyrazolo(1,5-a)pyrimidin-7-yl)-propylidene) phosphonic acid diethyl ester and acid salt Pyrazolo(1,5-a)pyrimidine is suspended in pyridine at 0° C. and treated with a solution of LiHMDS. After stirring at 0° C. for 30 minutes 1-(ethoxymethylphosphinyl)-1-ethenyl phosphonic acid, diethyl ester (hereinafter, EMP phosphonic acid) is added, the reaction warmed to 22° C., and stirred for 1 hour. It is then poured onto 10% HCl, extracted thrice with methylene chloride, dried with magnesium sulfate and stripped. The sample is purified by chromatography (ethyl acetate, ethyl acetate/acetone 3:1, 2:1, 1:1).

Refluxing the tetraester in concentrated hydrochloric acid for 12 hours and concentrating the solution synthesizes the corresponding acid.

Example 2

1-(Ethoxymethylphosphinyl)-(3-(3–Cyano-5-methyl-2-phenyl-pyrazolo(1,5-a)pyrimidin-7-yl)-propylidene)phosphonic acid diethyl ester 5,7-dimethyl-2-phenyl-pyrazolo(1,5-a)pyrimidine-3-carbonitrile in pyridine at 0° C. is treated with LiHMDS and stirred for 30 minutes. The deep red solution is treated with EMP phosphonic acid in THF. After stirring for 1 hour at 22° C., the reaction is poured onto 10% HCl. The organics are extracted with methylene chloride, then washed once each with 1N HCl, sodium bicarbonate, and brine, then dried with MgSO$_4$, and stripped. The sample is purified by chromatography.

Example 3

1-(Ethoxymethylphosphinyl)-(3-(3-Bromo-2,5-dimethyl-pyrazolo(1,5-a)pyrimidin-7-yl)-propylidene)phosphonic acid diethyl ester 3-Bromo-2,5,7-trimethyl-pyrazolo(1,5-a)pyrimidine is dissolved in THF at 0° C. and treated with LiHMDS. After stirring for 30 minutes, EMP phosphonic acid in THF is added. After stirring for 1 hour at 22° C., the reaction is poured onto 10% HCl. The organics are extracted with methylene chloride, then washed once each with 1N HCl, sodium bicarbonate, and brine, then dried with MgSO$_4$, and stripped. The sample is purified by chromatography.

Example 4

1-(Ethoxymethylphosphinyl)-(3-(3-Nitro-2,5-dimethyl-pyrazolo(1,5-a)pyrimidin-7-yl)-propylidene)phosphonic acid diethyl ester 2,5,7-Trimethyl-3-nitro-pyrazolo(1,5-a)pyrimidine is dissolved in pyridine at 0° C., then treated with LiHMDS. After stirring for 30 minutes, EMP phosphonic acid in THF is added. After stirring for 1 hour at 22° C., the reaction is poured onto 10% HCl. The organics are extracted with methylene chloride, then washed once each with 1N HCl, sodium bicarbonate, and brine, then dried with MgSO$_4$, and stripped. The sample is purified by chromatography.

Example 5

1-(Ethoxymethylphosphinyl)-(3-(2-Benzoyloxy-5-methyl-pyrazolo(1,5-a)pyrimidin-7-yl)-propylidene) phosphonic acid diethyl ester A) Cyanoacetohydrazide and 2,4 pentanedione are heated for 30 minutes in ethanol and acetic acid. The reaction is cooled to 22° C., then treated with 1N sodium hydroxide and refluxed for 15 minutes. The stirred hot flask is titrated to neutrality with 12N HCl, then cooled overnight at 0° C. The solid is collected and recrystallized from ethanol.

5,7-Dimethyl-pyrazolo[1,5-a]pyrimidin-2-ol in pyridine at 0° C. is treated with LiHMDS and stirred for 30 minutes. EMP phosphonic acid in THF is added and the reaction warmed to 22° C. for 1 hour. The reaction is extracted thrice with 1N sodium hydroxide and these are washed thrice with ethyl acetate. The aqueous fraction is brought to neutrality with 12N HCl, extracted thrice with ethyl acetate, washed with brine, dried with magnesium sulfate, and stripped. The material is used without further purification in the next reaction.

B) The crude pyrazolo[1,5-a]pyrimidin-2-ol in methylene chloride at 0° C. is treated with benzoyl chloride and triethyl amine. After stirring for 1 hour, the reaction is quenched with 1N HCl, extracted thrice with ethyl acetate, then washed with sodium bicarbonate, brine, dried with magnesium sulfate, and stripped. The sample is purified by chromatography (ethyl acetate, ethyl acetate/acetone 1:1).

Example 6

1-(Ethoxymethylphosphinyl)-(3-(2-Benzyloxy-5-methyl-pyrazolo(1,5-a)pyrimidin-7-yl)-propylidene) phosphonic acid diethyl ester 5,7-Dimethyl-pyrazolo[1,5-a]pyrimidin-2-ol, potassium carbonate, and DMF are heated to 115°–120° C. for 5 minutes, then treated with benzyl chloride. The reaction is stirred for 20 minutes at 120° C., then poured onto excess 1N NaOH. The organics are extracted twice with ethyl acetate, then washed with sodium bicarbonate and brine, dried with magnesium sulfate, and stripped to yield product.

The benzyl ether in THF at −78° C. is treated with LiHMDS and stirred for 30 minutes. EMP phosphonic acid in THF is added and stirred at 22° C. for 1 hour. The organics are poured onto 10% HCl, extracted thrice with ethyl acetate, washed with sodium bicarbonate and brine, dried with magnesium sulfate, and stripped. The product is isolated by chromatography (ethyl acetate, ethyl acetate/acetone 1:1).

Example 7

1-(Ethoxymethylphosphinyl)-(3-(2-Hexyloxy-5-methyl-pyrazolo(1,5-a)pyrimidin-7-yl)-propylidene) phosphonic acid diethyl ester 5,7-Dimethyl-pyrazolo[1,5-a]pyrimidin-2-ol, potassium carbonate, and DMF are heated to 115°–120° C. for 5 minutes, then treated with hexyl bromide. The reaction is stirred for 20 minutes at 120° C., then poured onto excess 1N NaOH. The organics are extracted twice with ethyl acetate, then washed with 1N HCl and brine, dried with magnesium sulfate, and stripped.

The crude ether is dissolved in THF, cooled to −78° C., and treated with LiHMDS. After stirring for 30 minutes, EMP phosphonic acid in a trace of THF is added and the reaction is stirred at 22° C. for 1 hour. The organics are poured onto 10% HCl, extracted thrice with ethyl acetate, washed with sodium bicarbonate and brine, dried with magnesium sulfate, and stripped. The product is purified by chromatography.

Example 8

1-(Ethoxymethylphosphinyl)-(3-(5-Methyl-2-phenyl-pyrazolo(1,5-a)pyrimidin-7-yl)-propylidene) phosphonic acid diethyl ester Pyrazolopyrimidine dissolved in pyridine is cooled to 0° C. and treated with LiHMDS and stirred for 30 minutes. A solution of EMP phosphonic acid in THF is added and the solution is stirred for an additional 30 minutes. The reaction mixture is poured into cold 10% HCl and washed three times with methylene chloride. The combined organic layers are washed with 10% HCl, $H_2O$, $NaHCO_3$, NaCl, dried with $MgSO_4$ and stripped to yield product. The product is purified by chromatography.

Example 9

1-(Ethoxymethylphosphinyl)-(3-(3-Iodo-5-methyl-2-phenyl-pyrazolo(1,5-a)pyrimidin-7-yl)-propylidene) phosphonic acid diethyl ester The compound from Example 8 (0.786 g, 1.5 mmol) is dissolved in chloroform (4.8 mL), is treated with N-Iodosuccinimide (0.345 g, 1.54 mmol) and refluxed for 20 minutes. The solution is cooled and poured onto 2N KOH (6.7 mL). The layers are separated and the chloroform is washed with water, dried with $MgSO_4$ and stripped. Purified by chromatography on silica gel with 2% ethanol/ethyl acetate to yield product.

Example 10

1-(Ethoxymethylphosphinyl)-(3-(3-Chloro-5-methyl-2-phenyl-pyrazolo(1,5-a)pyrimidin-7-yl)-propylidene)phosphonic acid diethyl ester The compound from Example 8 (1.490 g, 2.8 mmol) in chloroform (10 mL) is treated with N-Chlorosuccinimide (0.418 g, 3.1 mmol) and refluxed for 30 minutes. The solution is cooled and poured onto cold 2N KOH (13 mL). Separated and washed the organic layer twice with water and NaCl. Dried with $MgSO_4$ and stripped then chromatographed with 2% ethanol/ethyl acetate to form product.

Example 11

1-(Ethoxymethylphosphinyl)-(3-(3-Bromo-5-methyl-2-phenyl-pyrazolo(1,5-a)pyrimidin-7-yl)-propylidene)phosphonic acid diethyl ester The compound from Example 8 (1.488 g, 2.8 mmol) in chloroform (10 mL) is treated with N-Bromosuccinimide (0.52 g, 2.9 mmol) and the solution is refluxed for 25 minutes. Cooled and poured onto cold 2N KOH (13 mL) and separated. Washed organic layer twice with water and with brine. Dried with $MgSO_4$ and stripped then chromatographed with 2% ethanol/ethyl acetate to yield product.

Example 12

1-(Ethoxymethylphosphinyl)-(3-(3-Cyano-2,5-dimethyl-pyrazolo(1,5-a)pyrimidin-7-yl)-propylidene)phosphonic acid dimethyl ester Pyrazolo (1,5-a)pyrimidine in pyridine at 0° C. is treated with LiHMDS and stirred for 30 minutes. EMP phosphonic acid is added, the reaction warmed to 22° C. and stirred for 1 hour. The solution is poured onto 10% HCl, extracted thrice with methylene chloride, dried with magnesium sulfate and stripped to yield product.

Example 13

1-(Ethoxymethylphosphinyl)-(3-(2-(3-Methyl-4-oxo-6-phenyl14(3H)-pyrimidinyl))-propylidine) diphosphonic acid disodium salt 1-(Ethoxymethylphosphinyl)-(3-(2-(3-Methyl-4-oxo-6-phenyl4(3H)-pyrimidinyl))-propylidine)phosphonic acid diethyl ester is heated in concentrated hydrochloric acid at reflux for 24 hours, then the solution is stripped to dryness. The residue is suspended in water and the pH is adjusted to 7 with sodium hydroxide. The product is precipitated from the solution with methanol.

Example 14

1-(Ethoxymethylphosphinyl)-(3-(2-(4-Oxo-6-phenyl4(3H)-pyrimidinyl))-propylidine)phosphonic acid diethyl ester, The compound from Example 13, is dissolved in ethanol treated with Pearlman's catalyst and ammonium formate, then heated to reflux. After 1.5 hours, more catalyst and ammonium formate are added and the reaction continued for 4 more hours. The reaction is cooled to room temperature, filtered through celite, stripped then chromatographed on silica gel (ethyl acetate, acetone).

Other compounds can be prepared using the same procedure as above.

Example 15

1-(Ethoxymethylphosphinyl)-(3-(2-(3-Methyl-4-oxo-6-phenyl-4(3H)-pyrimidinyl))-propylidine) phosphonic acid diethyl ester sodium salt The compound from Example 14, is dissolved in methyl ethyl ketone (10 ml), treated with sodium iodide and heated to reflux overnight. The white precipitate is collected, washed with acetone and ether, then dried in the vacuum oven.

Example 16

1-(Ethoxymethylphosphinyl)-3-(3-methyl-6-phenyl14(3H)-pyrimidinone-2-yl)-propane phosphonic acid diethyl ester A 500-ml three-necked round-bottomed flask is flame-dried and cooled under nitrogen. To the flask is added 100 ml of anhydrous tetrahydrofuran. The flask is cooled in a dry ice/acetone bath and 100 ml of 1.6M n-butyllithium in hexane is added. When the addition is complete, 23.5 ml (24.5 g, 0.16 mmol) of diethyl methylphosphonate is added.

The reaction is stirred at −78° for 40 minutes and then at room temperature for 1 hour. The reaction is then quenched with 800 ml of 2N hydrochloric acid and the tetrahydrofuran is removed in vacuo. The residue is extracted with chloroform. The extracts are washed with brine and dried over anhydrous sodium sulfate. Removal of the solvent in vacuo affords 16.38 g of a clear, colorless liquid. The product is distilled to afford 11.49 g of (Ethoxymethylphosphinyl) methylphosphonic acid, diethyl ester having a boiling point of 148°–°150° at 2.5 mm of Hg.(Lit[6]127–130 at 1 mm of Hg). (55.6% yield).

A solution containing 11.4 g (44.15 mmol) of Ethoxymethylphosphinyl)methylphosphonic acid, diethyl ester 6.9 g (0.23 mmol) of paraformaldehyde and 5.02 g (48.57 mmol) of triethylamine is refluxed under nitrogen for 5 days. During the course of the reaction, an additional 8.4 g (0.30 mmol) of paraformaldehyde is added. The reaction is monitored by GC. The solvent is removed in vacuo and the residue is taken up in 500 ml of toluene. A trace of p-toluensulfonic acid is added and the solution is refluxed for 48 hours. The solvent is removed in vacuo and the residue chromatographed on 300 g of silica gel, slurry-packed in chloroform. The column is eluted with I% methanol in chloroform (2L), 2% methanol in chloroform (2L) and 3% methanol in chloroform (IL). Pure fractions are found by TLC analysis, combined and concentrated to afford 6.24 g of 1-(Ethoxymethylphosphinyl)-1-ethenyl phosphonic acid, diethyl ester (EMP phosphonic acid) as a colorless liquid (52.3% yield).

In a dry 50-ml two-necked round-bottomed flask under nitrogen are combined 221 mg of pyrimidinone and 5 ml of anhydrous tetrahydrofuran. The solution is cooled in a dry ice/acetone bath and is treated with 1.2 ml of a 1M solution of lithium bis(trimethylsilyl)amide in hexanes. The reaction is stirred at −78° for 30 minutes and 270 mg of 1-[(Ethoxymethylphosphinyl)]-1-ethenyl phosphonic acid, diethyl ester 13 b in 2 ml of tetrahydrofuran is added. The reaction is stirred at −78° for 40 minutes and then at 0° for 1 hour. Work up afforded 0.62 g of a yellow oil. The product is chromatographed to afford 383 mg of a white crystalline solid (81.5% yield) product.

The following Examples 17–26 are the pyrimidine bisphosphonate esters of Formula 3.

Example 17

(2-((4-(2-fluoro-6-nitrophenoxy)-6-methyl-2-pyrimidinyl)amino) ethylidene)bis(2,2'-(5,5-dimethyl-2,2'-dioxide-1,3,2-dioxaphosphorphinane))

Sodium hydride 50% in oil, (1.248 g, 26 mmol) was added to 2-fluoro-6-nitro phenol (4.085 g, 26 mmol) in DMF (20 mL) and stirred for 10 minutes at 22° C. 2-Amino4-chloro-6-methyl-pyrimidine (2.872 g, 20 mmol) was added, and the reaction stirred for 16 hours before quenching with water (150 mL). The resulting pyrimidine solid was collected and recrystallized from toluene with carbon: (2.69 g 10.8 mmol, 54%), mp 176° C. ($C_{10}H_9FN_4O_3$ 250.21)

Methylene bisphosphonic acid (12.8 g) is combined with methylene bis-(diethylphosphonate) (20.9 g) and the mixture is heated until the solid is completely dissolved (ca. 185° C.). Phosphorous pentachloride (121 g) is added to the solution (20-25° C.) in small portions over 1 hour. The mixture is stirred 30 minutes then diluted with hexane (300 ml) and stirred an additional 30 minutes. The mixture is filtered, the methylene bisphosphonylchloride solid is washed with cold hexane and dried briefly.

The crude tetra-acid chloride (methylene bisphosphonylchloride) is combined with 2.2-dimethyl-1,3-propanediol (17.5 g) in chlorobenzene (80 ml) and refluxed for 20 hours. The mixture is cooled and the solvent is removed under reduced pressure to give a solid. The solid is recrystallized from acetone to give the 2,2'-methylenebis(5, 5-dimethyl-2,2'-dioxide-1,3,2-dioxaphosphorinane), mp 193°–194° C.

The 2,2'-methylenebis(5,5-dimethyl-2.2'-dioxide 1,3,2-dioxaphosphorinane) (10.05 g) is dissolved in a warm solution of methanol (90 ml) containing paraformaldehyde (5.02 g) and diethylamine (3.3 ml) and gently refluxed for 2.5 hours. The mixture is cooled and the solvents removed by reduced pressure and mild heat. The residue is dissolved in toluene (40 ml) and a strongly acidic ion exchange resin is added and the mixture refluxed through a Dean-Stark trap for 80 minutes. The mixture is cooled and the solvents removed by reduced pressure with mild heat. The residue is recrystallized from acetone to give 2,2'-ethenylidenebis(5, 5-dimethyl-2,2'-dioxide-1,3,2-dioxaphosphorinane), mp 193°–194° C.

The pyrimidine (2.50 g, 10 mmol) and 2,2'-ethenylidenebis(5,5-dimethyl-2,2'-dioxide-1,3,2-dioxaphosphorinane) (3.576 g, 11 mmol) were stirred in toluene at reflux for 3 hours. After cooling, the solid was collected and recrystallized from toluene: 1.985 g (3.4 mmol, 34%). mp 178°–181° C.

Example 18

(2-((4-(2,4-difluorophenoxy)-6-methyl-2-pyrimidinyl)amino)ethylidene)bis(2,2'-(5,5-dimethyl-2,2'-dioxide-1,3,2-dioxaphosphorphinane))

Sodium hydride 50% in oil, (1.44 g. 30 mmol) was added to 2,4-difluoro phenol (2.86 g, 30 mmol) in DMF 20 mL and stirred for 10 minutes at 22° C. 2-Amino-4-chloro-6-methyl-pyrimidine (2.872 g, 20 mmol) was added, and the reaction stirred for 16 hours before quenching with water 150 mL. The resulting pyrimidine solid was collected and recrystallized from toluene: 2.69 g (10.8 mmol, 54%), mp 204°–205° C. ($C_{10}H_9F_2N_3O$ 237.13)

The pyrimidine 2.37 g, (10 mmol) and 2,2'-ethenylidenebis(5,5-dimethyl-2,2'-dioxide-1,3,2-dioxaphosphorinane) (3.567 g, 11 mmol) were stirred in toluene 20 mL at reflux for 4 hours. After cooling, the solvent was removed in vacuo, and the product purified by chromatography ethyl acetate/acetone 8:1 then a second time ethyl acetate/acetone 2:1): 1.68 g (2.99 mmol. 30%), mp 148°–151° C.

Example 19

(2-((4-(2-A-dibromophenoxy)-6-methyl-2-pyrimidinyl)amino)ethylidene)bis(2,2'-(5,5-dimethyl-2,2'-dioxide-1,3,2-dioxaphosphorphinane))

Sodium hydride 50% in oil, 1.44 g, (30 mmol) was added to 2,4-dibromo phenol 7.55 g. (30 mmol) in DMF 20 mL and stirred for 10 minutes at 22° C. 2-Amino-4-chloro-6-methylpyrimidine 2.872 g, (20 mmol) was added, and the reaction stirred for 16 hours before quenching with water 150 mL. The resulting pyrimidine solid was collected and recrystallized from toluene: 3.9 g (10.9 mmol, 54%), 206°–207° C. ($C_{10}H_9Br_2N_3O$ 358.99)

The pyrimidine 3.59 g, (10 mmol) and 2,2'-ethenylidenebis(5,5-dimethyl-2,2'-dioxide-1,3,2-dioxaphosphorinane) 3.567 g, (11 mmol) were stirred in toluene 20 mL at reflux for 16 hours. After cooling, the solid was collected and recrystallized from toluene, then from acetone: 620 mg (0.90 mmol, 9%), mp 184°–188° C.

Example 20

(2-((4-(4-cyanophenoxy)-6-methyl-2-pyrimidinyl) amino)ethylidene)bis(2,2'-(5,5-dimethyl-2,2'- dioxide-1,3,2-dioxaphosphorhinane))

Sodium hydride 50% in oil, 1.44 g, (30 mmol) was added to 4-cyano-phenol 3.57 g, (30 mmol) in DMF 20 mL and stirred for 10 minutes at 22° C. 2-Amino-4-chloro-6-methylpyrimidine 2.872 g, 20 mmol was added, and the reaction stirred for 16 hours before quenching with water 150 mL. The resulting pyrimidine solid was collected and recrystallized from toluene: 2.94 g 13 mmol, 65%, mp 212°–214° C. ($C_{11}H_{10}N_4O$ 226.19)

The pyrimidine 2,26 g, 10 mmol and 2,2'-ethenylidenebis (5,5-dimethyl-2,2'-dioxide-1,3,2-dioxaphosphorinane) 3.567 g, 11 mmol were stirred in toluene 20 mL at reflux for 16 hours. After cooling, the solid was collected and recrystallized from toluene, then from acetone: 2.3 g 4.18 mmol, 42%, mp 181°–183° C.

Sodium hydride 50% in oil, 1.44 g, 30 mmol was added to phenol 2.82 g, 30 mmol in DMF 20 mL and stirred for 10 minutes at 22° C. 2-Amino-4-chloro-6-methyl-pyrimidine 2.872 g, 20 mmol was added, and the reaction stirred for 16 hours before quenching with water 150 mL. The resulting pyrimidine solid was collected and recrystallized from toluene to give 2,2'-ethenylidenebis(5,5-dimethyl-2,2'-dioxide-1,3,2-dioxaphosphorinane): 2.82 g 14 mmol, 70%, mp 193°–194° C. $C_{11}H_{10}N_3O$ 201.07

The pyrimidine 1.00 g, 5 mmol and 2,2'-ethenylidenebis (5,5-dimethyl-2.2'-dioxide-1,3,2-dioxaphosphorinane)

The pyrimidine 1.00 g, 5 mmol and 2,2'-ethylidenebis(5, 5-dimethyl-2,2'-dioxide-1,3,2-1.50 g, 5 mmol were stirred in toluene 5 mL at reflux for 72 hours. After cooling, the reaction was diluted with water, extracted thrice with methylene chloride, dried with $MgSO_4$, and stripped. The sample was chromatographed ethyl acetate/acetone 2:1:1.36 g 2.7 mmol, 54%.

Example 21

(2-((4-(4-morpholinyl)-6-methyl-2-pyrimidinyl) amino)ethylidene)bis(2,2'-(5,5-dimethyl-2,2'- dioxide-1,3,2-dioxaphosphorhinane))

2-Amino-4-chloro-6-methyl-pyrimidine 2.87 g. 20 mmol and morpholine 1.75 g. 20 mmol were refluxed in water 35 mL for 2 hours, then cooled to 22° C. and con HCl 15 mL was carefully added. Heating was continued for 1 hour at reflux, then the yellow solution was cooled and water 140 mL added. 50% Sodium hydroxide was added until a white precipitate appeared. The pyrimidine was collected and recrystallized from water: 1.74 g, 9.0 mmol, 45%, mp 174°–175° C. $C_9H_{14}N_4O$ 194.23

The pyrimidine 1.64 g, 8.4 mmol and 2,2'-ethenylidenebis (5,5-dimethyl-2,2'-dioxide-1,3,2-dioxaphosphorinane) 3.03 g, 9.35 mmol were stirred in toluene 20 mL at reflux for 5 hours. After cooling, the solid was collected and recrystallized from acetone: 1.98 g 3.8 mmol, 45%, mp 168°–172° C.

Example 22

(2-((4-(4-piperidinyl)-6-methyl-2-pyrimidinyl) amino)ethylidene)bis(2,2'-(5,5-dimethyl-2,2'- dioxide-1,3,2-dioxaphosphorhinane))

Sodium acetate 16.8 g and acetic acid 0.25 mL in water 40 mL were treated with 2-Amino-4-chloro-6-methyl-pyrimidine 2.871 g, 20 mmol and piperidine 1.72 g, 20 mmol, then heated to reflux for 2 hours. The pH was adjusted to 10 with 50% NaOH and the reaction was allowed to stand for 16 hours. The yellow orange precipitate was collected, treated with con HCl 10 mL for 1 hour at 100° C., then cooled. 50% Sodium hydroxide was added until precipitation began. The crude pyrimidine was collected and recrystallized from toluene: 1.55 g 8.0 mmol, 56%, mp 188°–189° C. $C_{11}H_{16}N_4$ 193.22

2,2'-ethenylidenebis(5,5-dimethyl-2,2'-dioxide-1, 3,2-dioxaphosphorinane) 2.853 g, 8.8 mmol and the pyrimidine 1.55 g, 8 mmol were heated in refluxing toluene for 22 hours. Additional 2,2'-ethenylidenebis(5,5-dimethyl-2,2'- dioxide-1,3,2-dioxaphosphorinane) 0.519 g, 1.6 mmol was added and reflux maintained for 3 hours. Upon cooling a white solid precipitated, which was collected and recrystallized from acetone: 2.40 g 4.6 mmol, 58%, mp 174°–178° C.

Example 23

(2-((4-(3-chlorophenoxy)-6-methyl-2-pyrimidinyl) amino)ethylidene)bis(2,2'-(5,5-dimethyl-2,2'- dioxide-1,3,2-dioxaphosphorhinane))

Sodium methoxide 25% by weight, 4.58 mL, 20 mmol in methanol 20 mL was treated with thiophenol 2.05 mL, 20 mmol and 2-Amino-3-chloro-6-methyl-pyrimidine 2.87 g. 20 mmol and heated at reflux for 2 hours. Upon cooling a white pyrimidine solid precipitated, which was filtered, washed with water, and recrystallized from toluene: 3.5 g 16.1 mmol, 81%. mp 186°–187° C. $C_{11}H_{11}N_3S$ 217.25.

2,2'-ethenylidenebis(5,5-dimethyl-2,2'-dioxide-1, 3,2-dioxaphosphorinane) 3.93 g, 11.5 mmol and the pyrimidine 2.5 g, 11.5 mmol were added to toluene 20 mL and refluxed for 16 hours. The reaction was stripped on the rotovap. The solid was washed with hexane, filtered, dried in the oven, then dissolved in hot ethyl acetate 100 mL, filtered and stripped. Numerous attempts to recrystallize this material failed to result in pure material. The solid was then chromatographed acetonitrile:methanol 10:1: 250 mg 0.45 mmol, 4%, mp 176°–178° C.

Example 24

(2-((4-(3,4-dichlorophenoxy)-6-methyl-2- pyrimidinyl)amino)ethylidene)bis(2,2'-(5,5- dimethyl-2,2'-dioxide-1,3,2-dioxaphosphorhinane))

Sodium hydride 50% in oil, 1.44 g, 30 mmol was added to 3,4-dichlorophenol 4.89 g, 30 mmol in DMF 20 mL. The reaction mixture was stirred at 22° C. for 30 minutes. 2-Amino-4-chloro-6-methyl-pyrimidine 2.87 g, 20 mmol was then added and the mixture was heated to reflux and stirred for 3 hours. The reaction was allowed to cool and was then added to water 100 mL. The resulting white pyrimidine solid was filtered and recrystallized from toluene: 1.53 g 5.7 mmol, 29%, mp 223°–224° C. $C_{11}H_9Cl_2N_3O$ 270

The pyrimidine 1.52 g, 5.63 mmol and 2,2t-ethenylidenebis(5,5-dimethyl-2,2t-dioxide-1,3,2- dioxaphosphorinane) 2.01 g, 6.19 mmol were added to toluene 20 mL and refluxed for 16 hours. The reaction mixture was allowed to cool and was then stripped to yield a crude, orange solid. The solid was recrystallized twice from toluene/charcoal but impurities remained. It was then recrystallized twice from acetone to yield a pure, white solid: 130 mg 0.22 mmol, 4% mp 169°–171° C.

Example 25

(2-((4-(2,4-dichlorophenoxy)-6-methyl-2- pyrimidinyl)amino) ethylidene)bisphosphonic acid, tetraethyl ester The ethenylidene bisphosphonate (10.0 g, 33.3 mmol) and the 2-aminopyrimidine (8.99 g, 33.3 mmol) in toluene (30 mL) were stirred in a sealed vessel at 95° C. for 38 hours. After cooling to 22° C., the reaction was diluted with water, extracted 3×$CH_2Cl_2$, dried ($MgSO_4$), and concentrated to an orange oil, 18.68 g. Chromatography on silica gel with 3% MeOH in $CH_2Cl_2$ gave the white solid, m.p. 76°–77° C.: 9.1 g (15.6 mmol, 48%).

Example 26

(2((4-(methyl)-6-methoxy-2-pyrimidinyl)amino) ethylidene)bis(2,2'-(5,5-dimethyl-2,2'-dioxide-1,3,2-dioxaphosphorhine))

Sodium methoxide (25% by weight, 9.1 mL, 40 mmol) was dissolved in methanol (60 mL), treated with 2-Amino-4-chloro-6-methyl-pyrimidine (2.87 g, 20 mmol), then refluxed for 16 hours. After cooling, the solid was collected, washed with methanol, then recrystallized from methyl t-butyl ether: 910 mg (6.54 mmol, 33%), mp 158°–159° C.

The pyrimidine (800 mg, 5.75 mmol) and 2,T-ethenylidenebis(5,5-dimethyl-2,2'-dioxide-1,3.2-dioxaphosphorinane) (2.10 g, 6.5 mmol) were stirred in toluene (20 mL) at reflux for 4 hours. After cooling, the solid was collected and recrystallized from methylene chloride/hexane, toluene, and finally from acetone: 900 mg (1.94 mmol, 34%), mp 169°–171° C.

What is claimed:

1. A compound of Formula 1 or 2 or pharmaceutically acceptable salts thereof

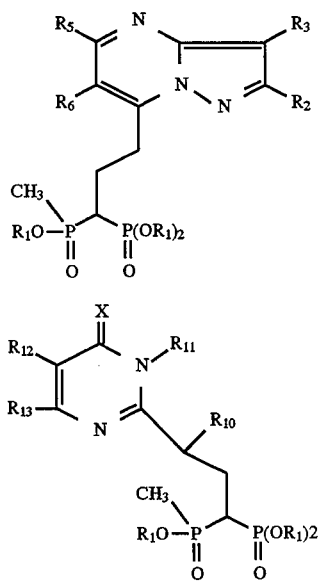

FORMULA 1

FORMULA 2 wherein X is O or S;

each occurrence of $R_1$ is the same or different and is selected from the group consisting of H, Na, K, tromethamine, $C_1$–$C_6$ alkyl, $CH_2$-phenyl, phenyl (optionally substituted with 1 to 5 $NO_2$, halo, or $C_1$–$C_4$ alkyl), or both $R_1$'s on the same phosphorus atom taken together are —$CH_2$—$CH_2$—, —$CH_2$—$CH_2$—$CH_2$—, or —$CH_2$—$C(CH_3)_2$—$CH_2$— whereby a heterocyclic ring is formed;

$R_2$ is hydrogen, $C_1$–$C_6$ alkyl, benzoyloxy, benzyloxy, $C_1$–$C_6$ alkoxy, phenoxy, $C_3$–$C_7$ cycloalkyl, phenyl (optionally substituted with 1 or 2 phenyls, or 1 to 5 halo, $NO_2$, CN, $CF_3$, $C_1$–$C_{10}$ alkyl, $C_3$–$C_7$ cycloalkyl, $C_1$–$C_6$ alkoxy or $C_1$–$C_6$ alkylthio), 2-, 4- or 5-pyrimidyl (optionally substituted with 1 or 2 phenyls, or 1 to 3 halo, $NO_2$, CN, $CF_3$, $C_1$–$C_{10}$ alkyl, $C_3$–$C_7$ cycloalkyl, $C_1$–$C_6$ alkoxy, or $C_1$–$C_6$ alkylthio), 2-, 3- or 4-pyridyl (optionally substituted with 1 or 2 phenyl 1 to 4 halo, $NO_2$, CN, $CF_3$, $C_1$–$C_{10}$ alkyl, $C_3$–$C_7$ cycloalkyl, $C_1$–$C_6$ alkoxy or $C_{C6}$ alkylthio), 1-, or 2-naphthalenyl (optionally substituted with 1 or 2 phenyls, or 1 to 7 halo, $NO_2$, CN, $CF_3$, $C_1$–$C_{10}$ alkyl, $C_3$–$C_7$ cycloalkyl, $C_3$–$C_6$ alkoxy or $C_1$–$C_6$ alkylthio);

$R_3$ is H, CN, $CO_2R_1$, $COR_2$, $CON(R_5)_2$, halo, $NO_2$, CN, $CF_3$, $C_1$–$C_{10}$ alkyl, $C_3$–$C_7$ cycloalkyl, or phenyl;

$R_5$ is H, $C_1$–$C_6$ alkyl or $C_3$–$C_7$ cycloalkyl;

$R_6$ is H, halo, or $C_1$–$C_6$ alkyl;

$R_{10}$ is H, $C_1$–$C_6$ alkyl, $C_3$–$C_7$ cycloalkyl, or phenyl (optionally substituted with 1 or 2 phenyls, or 1 to 5 halos, $NO_2$, CN, $CF_3$, $C_1$–$C_{10}$ alkyl, $C_3$–$C_7$ cycloalkyl, $C_1$–$C_6$ alkoxy or $C_1$–$C_6$ alkylthio);

$R_{11}$ is H, $C_1$–$C_6$ alkyl, $C_3$–$C_7$ cycloalkyl, allyl, $CH_2OR_{14}$, $CH_2$-phenyl, or phenyl (optionally substituted with 1 to 5 $NO_2$, halos, or $C_1$–$C_4$ alkyl);

$R_{12}$ is H, $C_1$–$C_6$ alkyl, halo, $NO_2$;

$R_{13}$ is hydrogen, $C_1$–$C_6$ alkyl, $C_3$–$C_7$ cycloalkyl, or phenyl (optionally substituted with 1 to 2 phenyls, or 1 to 5 halos, $NO_2$, CN, $CF_3$, $C_1$–$C_{10}$ alkyl, $C_3$–$C_7$ cycloalkyl, $C_1$–$C_6$ alkoxy or $C_1$–$C_6$ alkylthio), 2-, 3- or 4-pyridyl (optionally substituted with 1 to 2 phenyls, or 1 to 4 halos, $NO_2$, CN, $CF_3$, $C_1$–$C_{10}$ alkyl, $C_3$–$C_7$ cycloalkyl, $C_1$–$C_6$ alkoxy or $C_1$–$C_6$ alkylthio), 1- or 2-(optionally substituted with 1 to 2 phenyls, or 1 to 7 halos, $NO_2$, CN, $CF_3$, $C_1$–$C_{10}$ alkyl, $C_3$–$C_7$ cycloalkyl, $C_1$–$C_6$ alkoxy or $C_1$–$C_6$ alkylthio), piperidinyl, morpholinyl, pyrrolidinyl, $N(R_5)_2$, $NHC(O)R_{14}$ or $NHC(O)OR_{14}$; and $R_{14}$ is $C_1$–$C_6$ alkyl, $C_3$–$C_7$ cycloalkyl, allyl, $CH_2$-phenyl, or phenyl (optionally substituted with 1 to 5 $NO_2$, halos, or $C_1$–$C_4$ alkyl).

2. The compound of claim 1 wherein said $R_1$ is ethyl.

3. The compound of claim 1 wherein said $R_2$ is methyl, hydrogen or phenyl.

4. The compound of claim 1 wherein said $R_3$ is CN, phenyl, $NO_2$, hydrogen or halo.

5. The compound of claim 1 wherein said $R_5$ is methyl.

6. The compound of claim 1 wherein said $R_6$ is hydrogen.

7. The compound of claim 1 wherein X is oxygen.

8. The compound of claim 1 wherein $R_{10}$ is hydrogen.

9. The compound of claim 1 wherein $R_{11}$ is a $C_1$–$C_3$ alkyl.

10. The compound of claim 1 wherein $R_{13}$ is a phenyl.

11. The compound of claim 7 wherein said $R_{13}$ is a phenyl and is substituted with a halo, methyl, methoxy or $CF_3$.

12. The compound of claim 1 of Formula 2 which is 1-(Ethoxymethylphosphinyl)-3(3-methyl-6-phenyl-4-(3H)-pyrimidinone-2-yl)-propane phosphonic acid diethyl ester.

13. A method for treating inflammation comprising the administration of a therapeutically effective amount of a compound of Formula 1 or 2 to a patient in need thereof.

14. The method of claim 13 wherein said compound is administered to a patient in need thereof in an anti-inflammatory effective amount of from 0.001 mg to 1.0 gram and is administered orally, intramuscularly, intravenously, transdermally, intra-articularly, subcutaneously, or intraperitoneally.

* * * * *